US008252607B2

(12) United States Patent
Gupta et al.

(10) Patent No.: US 8,252,607 B2
(45) Date of Patent: Aug. 28, 2012

(54) BIO-COMPATIBLE HYBRID ORGANIC/INORGANIC GELS: VAPOR PHASE SYNTHESIS

(76) Inventors: Gautam Gupta, Albuquerque, NM (US); Gabriel Lopez, Albuquerque, NM (US); Plamen Atanassov, Albuquerque, NM (US)

( * ) Notice: Subject to any disclaimer, the term of this patent is extended or adjusted under 35 U.S.C. 154(b) by 1055 days.

(21) Appl. No.: 12/134,874

(22) Filed: Jun. 6, 2008

(65) Prior Publication Data
US 2008/0311391 A1    Dec. 18, 2008

Related U.S. Application Data

(60) Provisional application No. 60/933,402, filed on Jun. 6, 2007.

(51) Int. Cl.
*G01N 33/552* (2006.01)
(52) U.S. Cl. ........ 436/527; 436/149; 436/164; 436/172; 436/174; 436/518; 436/524; 436/805; 436/809; 422/82.11; 422/52; 422/82.05; 422/82.08; 422/82.09; 422/407; 422/420; 435/164; 435/165; 435/283.1; 435/287.1; 435/287.2; 435/4; 435/5; 435/7.2; 435/7.9; 435/182; 435/6.1; 252/502; 423/338; 427/69; 428/336; 428/446; 506/16; 712/10
(58) Field of Classification Search .................. 422/102, 422/52, 82.05, 82.08, 82.09, 82.11, 99, 407, 422/420; 435/164, 165, 283.1, 287.1, 287.2, 435/4, 5, 7.2, 7.9, 182, 6.1; 436/149, 164, 436/172, 174, 518, 805, 809, 524, 527; 252/502; 423/338, 70.16; 427/69; 428/336, 446; 506/16; 712/10
See application file for complete search history.

(56) References Cited

U.S. PATENT DOCUMENTS

| 5,420,081 A * | 5/1995 | Mattes et al. ................ 501/12 |
| 6,284,163 B1 * | 9/2001 | Stowell et al. ............... 264/4.1 |
| 6,303,290 B1 | 10/2001 | Liu et al. |
| 2006/0134050 A1 | 6/2006 | Griffith et al. |

FOREIGN PATENT DOCUMENTS

KR    10/2005-0017922 A    2/2005

OTHER PUBLICATIONS

Eglin et al, "Type I collagen, a versatile liquid crystal biological template for silica structuration from nano- to microscopic scales" Soft Matter, 2005, 1: pp. 129-131.*
Kandimalla et al, "Immobilization of Biomolecules in Sol-Gels: Biological and Analytical Applications" Critical Reviews in Analytical Chemistry, 36:73-106, 2006, pp. 73-106.* Podbielska et al, "Sol-gel technology for biomedical engineering" Bulletin of the Polish Academy of Sciences, vol. 53, No. 3, 2005.*
Ismail et al, "Alkali treatment of dye-doped sol-gel glass films for rapid optical pH sensing" The Analyst, 2002, 127, pp. 253-257.*
Gautier et al,"Sol-gel encapsulation extends diatom viability and reveals their silica dissolution capability" Chem. Commun., 2006, pp. 4611-4613.*
Carturan,"Encapsulation of functional cells by sol-gel silica: actual progress and perspectives for cell therapy" Journal of Materials Chemistry, 2004, 14: pp. 2087-2098.*

* cited by examiner

*Primary Examiner* — Dennis M White
(74) *Attorney, Agent, or Firm* — Gonzales Patent Services; Ellen M Gonzales

(57) ABSTRACT

The disclosure provides a simple and effective way of synthesizing robust organic-inorganic hybrid gels and ultra-thin films using vaporization of a gel precursor. The gels are synthesized at relatively low temperature allowing the activity of the immobilized species to be maintained. The disclosure provides robust, synthetic, selective, active and/or passive transport systems in the form of functional biologically active species and mechanisms for forming them. These systems allow selective and passive or active transport of ionic, molecular and biological species through the incorporation of functional biological molecules and biomolecular assemblies in a rigid matrix.

39 Claims, 10 Drawing Sheets

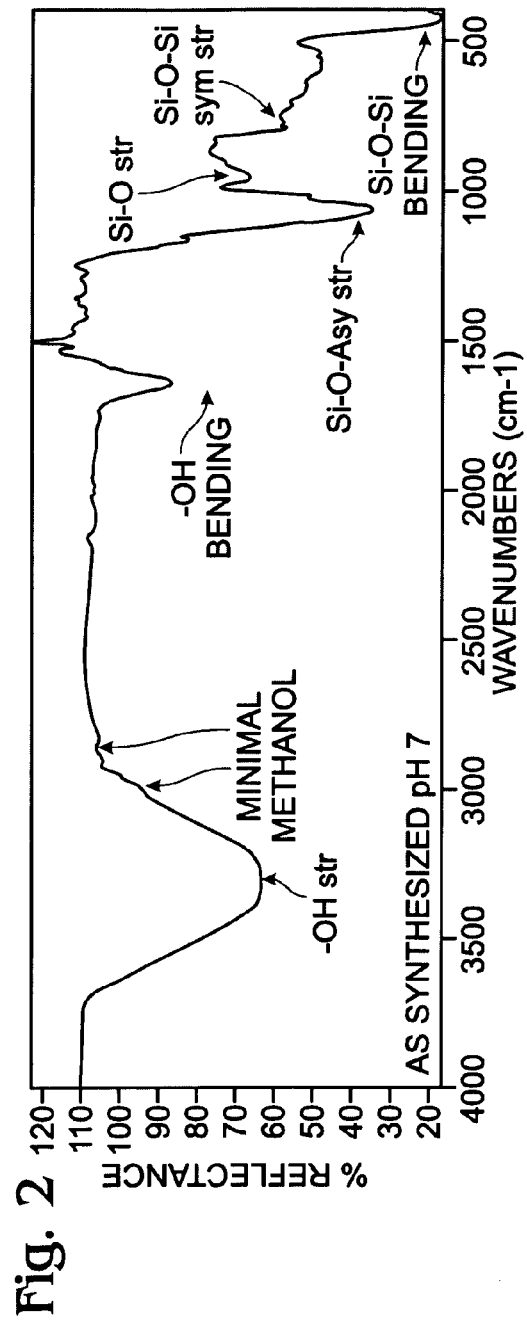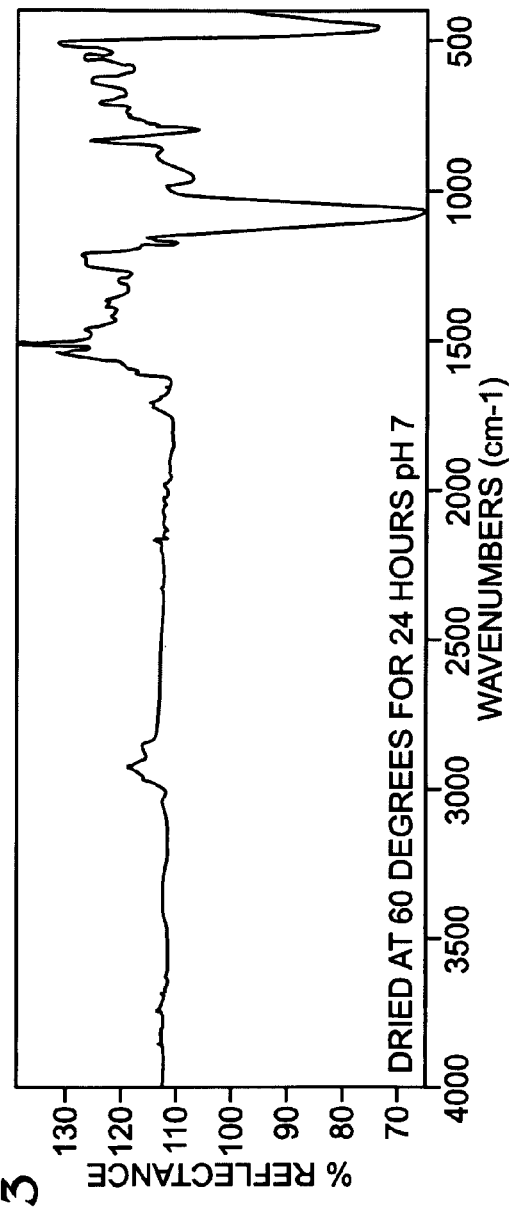

TMOS GEL

BIO-COMPATIBLE HYBRID ORGANIC/INORGANIC GELS: VAPOR PHASE SYNTHESIS

PRIORITY CLAIM

The present invention claims priority to U.S. Provisional Patent Application Ser. No. 60/933,402, filed Jun. 6, 2007, the entirety of which is hereby incorporated by reference.

FEDERALLY SPONSORED RESEARCH

The present invention was made with government support under Grant No. ARO-DAAD-19-03-1-0173 and W911NF-06-1-0333 awarded by the Army Research Office. The U.S. Government has certain rights in the invention.

BACKGROUND AND SUMMARY

Ever since the discoveries of black lipid membranes, liposomes, and solid supported membranes, extensive work has been done in all these three fields. Emulating the structural and functional complexities of a biological membrane at a substrate surface is perhaps one of the most persistent challenges of modern materials chemistry because of the fragility and long term instability of the phospholipid PBMs.

In order to provide sufficient robustness, many synthetic gels incorporate silica. A disadvantage of previously described mechanisms for forming synthetic gels is that the mechanisms typically required significant amounts of an organic co-solvent such as ethanol, in order to dissolve silica precursors. Moreover, such mechanisms frequently additionally use an acid such as Hydrochloric acid (HCl) as a catalyst. However, solvents and acids such as ethanol and HCl are harmful to biological species, and make it difficult, if not impossible, to form membranes incorporating functional biologically active species.

The present disclosure provides the synthesis of robust synthetic selective and active transport systems in the form of functional biologically active species (including, for example, liposomes, cells, enzymes, proteins, light harvesting complexes, etc., entrapped or encapsulated in gels. These systems allow selective and passive or active transport of ionic, molecular and biological species through the incorporation of functional biological transport molecules in a rigid matrix. Robustness may be imparted, for example, by inorganic silica in between multilamellar layers of lipids. These active transport systems may then be incorporated into various mechanism and for a variety of purposes including, for example, nanofluidic devices, biosensors, drug-delivery, biofuel cells (enzymatic, whole cell), micro reactors (cells), separations and photonic devices.

BRIEF DESCRIPTION OF THE DRAWINGS

FIG. 2 is a graph depicting the FTIR spectrum of a gen synthesized according to an exemplary method of the present invention.

FIG. 3 is a graph depicting the FTIR spectrum of the gel of FIG. 2 after it has been dried for 24 hours.

FIG. 4C is a SEM micrograph of a dried gel synthesized at pH 10.

DETAILED DESCRIPTION

Various embodiments of the present disclosure provide robust, synthetic, selective, active and/or passive transport systems in the form of versatile membranes which, in some embodiments, incorporate functional biological species such as, for example, liposomes or cells, entrapped in gels. The present disclosure further provides mechanisms for synthesizing these active transport systems. The active transport systems described herein may then be incorporated into various mechanism including, for example, nanofluidic devices. These systems allow selective and passive or active transport of ionic, molecular and biological species through the incorporation of functional biological transport molecules in a rigid matrix. Robustness may be imparted, for example, by inorganic silica and multi-lamellar or hexagonal arrangements of lipids. For the purposes of the present disclosure, the term "functional" in the context of an active transport system means that the transmembrane proteins and peptides are able to perform upon stimulation or excitation.

Figure 1:
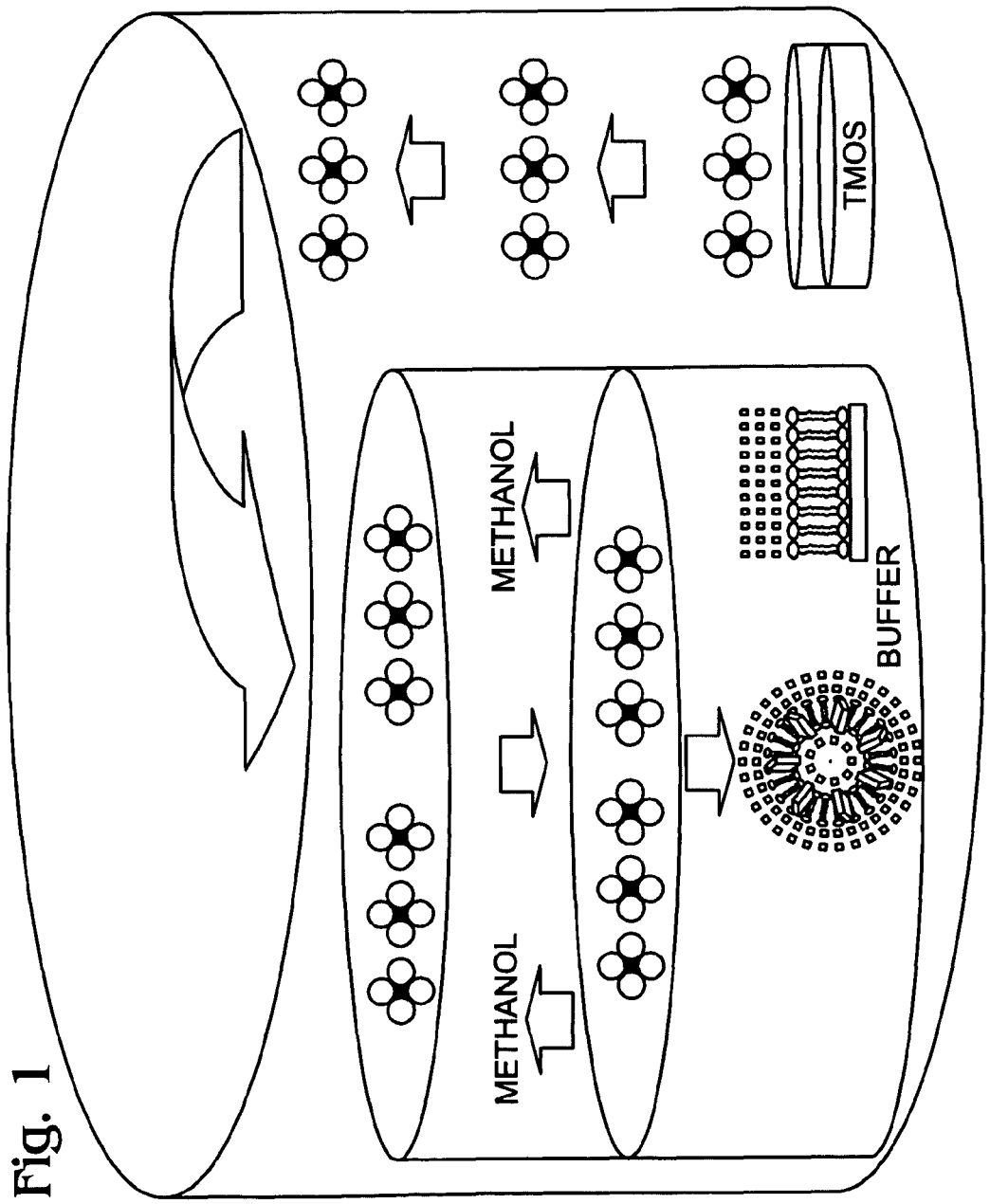
FIG. 1 is a schematic illustration of an exemplary method according to one embodiment of the present invention.
Figure 4A:
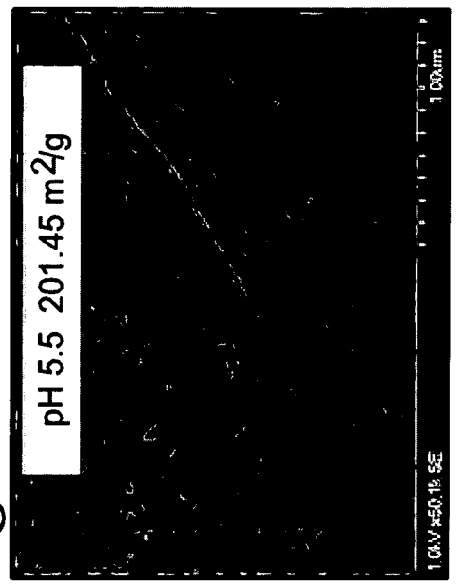
FIG. 4A is a SEM micrograph of a dried gel synthesized at pH 2.
Figure 4B:
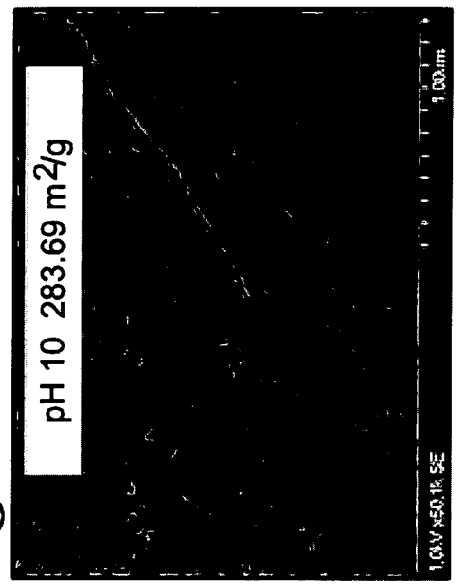
FIG. 4B is a SEM micrograph of a dried gel synthesized at pH 5.5.
Figure 4C:
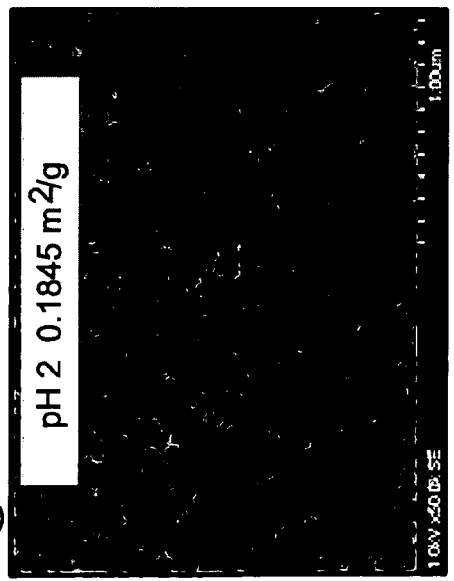
FIG. 4C is a SEM micrograph of a dried gel synthesized at pH 7.
Figure 4D:
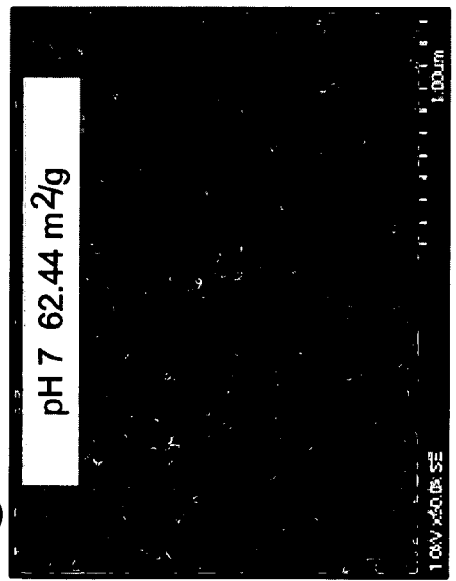

According to a first embodiment, the present disclosure provides a novel method of preparing biocompatible hybrid gels. Turning to FIG. 1, a schematic representation of an exemplary method is provided which demonstrates a one-step approach for forming silica gels using a vaporization technique. As shown in FIG. 1, an aqueous solution which may be, for example, a buffer containing a desired biological species, is placed next to a vial containing a gel precursor in a closed container at a suitable temperature. Exemplary gel precursors including tetramethoxy silane (TMOS), tetraethoxy silane (TEOS), Acrylic acid and other monomers, volatile organic or inorganic precursors such as metal alkoxy silanes, and metal chlorides such as Ticl4, Sicl4, etc. TMOS is relative volatile at 37° C., accordingly, 37° C. may be a suitable temperature for conducting the procedure. However, as will be evident in reviewing this disclosure, other temperatures may be used for a variety of reasons. Under the aforementioned, or other, suitable, conditions the gel precursor evaporates and is exposed to the buffer. According to various embodiments, the precursor may be delivered to the buffer by saturation, aerosol delivery, use of a nebulizer, ultrasonication, or other suitable means. Upon mixing with the buffer, the gel precursor is hydrolyzed. For example, TMOS hydrolyzes to silicon hydroxide and methanol. However, the relatively slow rate of transfer of the precursor leads to minimal methanol presence in the system at any given time. Upon further condensation silicon dioxide is formed and leads to formation of gel, as demonstrated by the equations below:

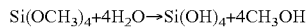

$$Si(OCH_3)_4 + 4H_2O \rightarrow Si(OH)_4 + 4CH_3OH$$

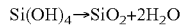

$$Si(OH)_4 \rightarrow SiO_2 + 2H_2O$$

Figure 20:
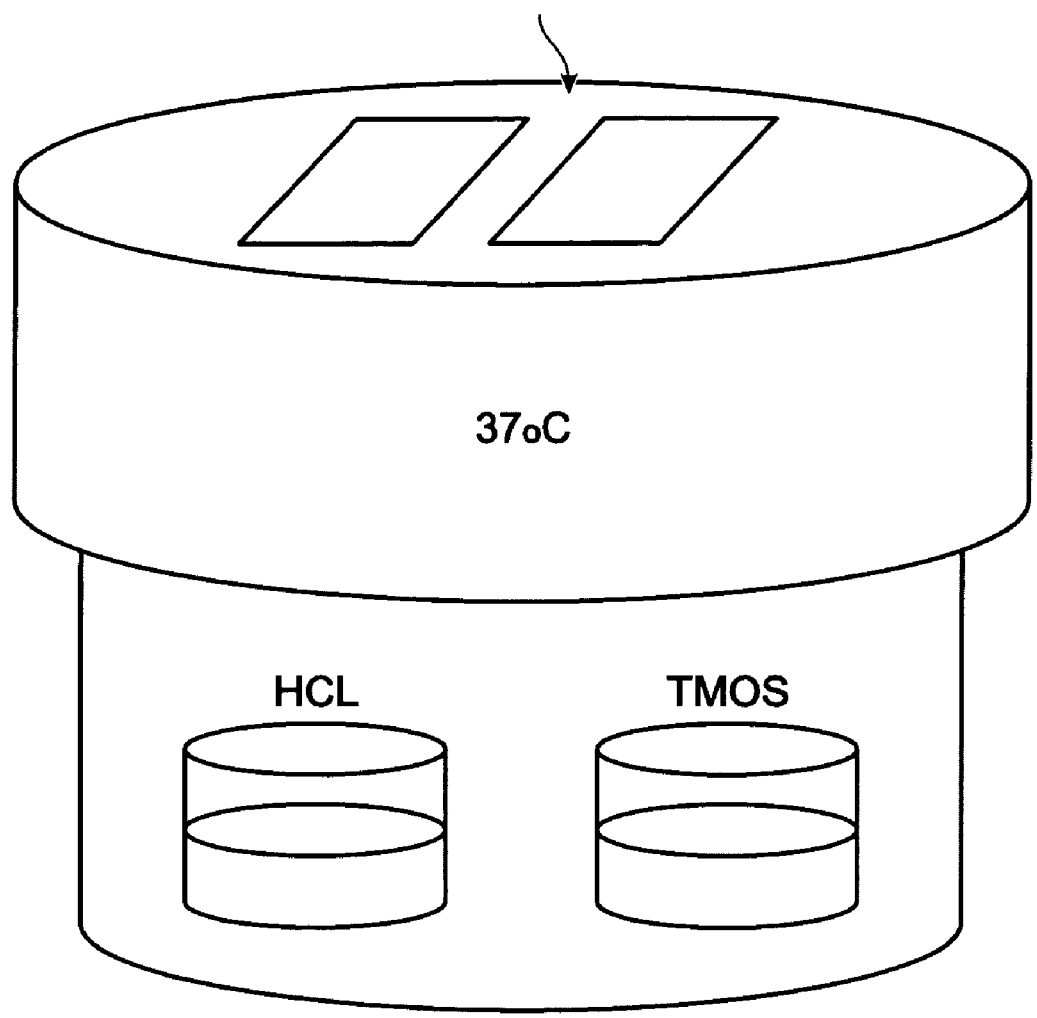
FIG. 20 is a schematic illustration of another method according to an embodiment of the present invention.

If desired, the lipid assemblies can then be spin-coated on wafers using techniques well known to those of skill in the art and as shown in FIG. 20. These lipid assemblies may or may not include transmembrane proteins and/or peptides, as desired. These multi-lamellar lipid assemblies can be exposed to vapors of TMOS/TEOS and water leading to formation of different structures.

As stated above, the gels may be formed at 37° C., alternatively, the gels may be formed at other temperatures, including, for example, room temperature. In general, higher temperatures will result in a shorter gelation time and lower temperatures will result in a longer gelation time. According to some embodiments, the typical gelation time for room temperature synthesis of pH 7 buffer is around 6 hours.

Using the above-described technique, it is possible to form precise structures, e.g., lamellar or hexagonal structures, entrapped liposomes, etc., in silica materials, by making simple variations to the basic procedure, as described in greater detail below and as shown in the various examples.

FIG. 2 shows the FTIR spectrum of a gel synthesized according to an embodiment of the presently-described methods at pH 7. The peaks clearly indicate the formation of Si—O—Si linkages. These gels show the presence of water and very little methanol. The Si—O—Si and Si—OH peaks are clearly visible. FIG. 3 shows an FTIR spectrum of the gel dried at 60° C. for 24 hrs at pH 7. The slight presence of Si—OH that had been seen in the previous FTIR spectrum is decreased due to further condensation. Furthermore, the Si—O—Si symmetric stretch and Si—O—Si bending are increased after heating. Water is almost eliminated at this point and the samples appear as transparent or translucent glass.

Using the techniques described herein, gels may be synthesized at any desired pH and ionic strength. FIGS. 4A-4D show the SEM micrograph of a dried gel synthesized at different pHs. The hydrolysis of precursors is affected by the use of catalyst. The first step of hydrolysis in acid catalyzed conditions, which is the conversion of $Si(OCH_3)_4$ to $(CH_3O)_3$Si—OH is rapid, where as further protonation of the product is less favorable due to the removal of the electron donating methoxy group. Therefore condensation reactions occur between Si—OH and protonated Si—OCH$_3$. The terminal Si—OCH$_3$ is more reactive, thus leading to the formation of linear polymers. Cross linking of these linear chains yields relatively homogeneous gels with small pores. On the other hand, above the iso-electric point of silica (pH 2.2) the base catalysis proceeds faster when the electron donating group —OCH$_3$ is removed. This leads to the formation of fully hydrolyzed monomers, which leads to cross-linking at early stages. Due to higher condensation rates and inter-linking of highly cross-linked polymers, a porous network is formed and gelation occurs relatively quickly.

Figure 5:
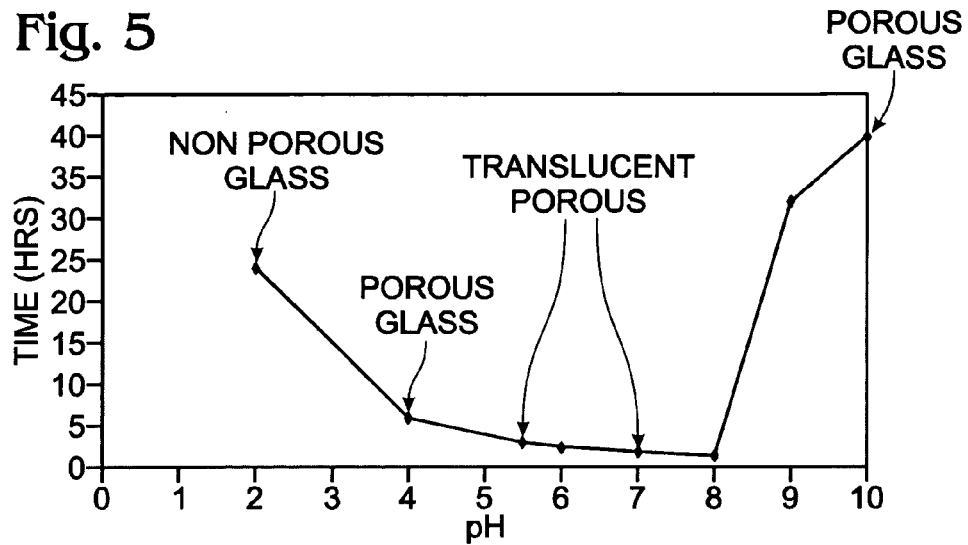
FIG. 5 is a graph depicting the gelation time of gels at synthesized at various pH levels.

FIG. 5 shows the gelation time of the gels at various pH levels. Hydrolysis and condensation both play an important role in formation of gels. Gel times decrease between pH 2 and pH 7. This is because the condensation rate is proportional to $[OH]^-$ and the solubility of silica is low in this pH range. Above pH 7 the condensed species tend to be ionized and therefore repulsive in nature. This, in addition to the high solubility of silica, results in longer gel times. Moreover, salt concentrations also effect the gelation time. In this case, salt provides shielding to electrostatic repulsions, leading to shorter gelation times. If desired, shorter gelation times can be obtained by sonication of the precursor. Accordingly, thin films can be gelled in a matter of minutes using the techniques described herein. Accordingly, the process described herein is extremely amenable to alterations in experimental conditions including, but not limited to changes in pH, temperature, salt, or gelation time.

It will be appreciated that the process may be performed to completion, that is until the gel is completely formed, or performed to partial-completion, that is, the process may stop or be stopped before the gel is completely formed, resulting in a partial gel formation. In this case, the partially formed gel may be subjected to further processing, for example, it may be spin coated onto a substrate such as a wafer, dip coated onto a substrate, spray coating onto a substrate, particle formation, such as by spray drying and other methods disclosed in U.S. patent application Ser. Nos. 10/640,249 and 12/015,412 and U.S. Provisional Patent Application No. 60/985,050, each of which are hereby incorporated by reference.

Furthermore, gels with variable surface (i.e. porosity) can be formed, either by using a different pH, or by varying the amount of exposure to TMOS precursor, as shown below in Table I. For example, in base catalyzed reactions, highly cross-linked large sol particles are initially obtained which eventually link to form gels with large pores between the inter-connected particles due to higher condensation rates and the formation of more branched-like structures. At pH 2, the rate or condensation is slow, thus leading to relatively non-porous gels. The relatively non-porous gels are generally transparent in appearance while more porous materials may be translucent or even in the form of powder. However, should a transparent gel be desirable, any material formed using the above-described method can take on this appearance if it is exposed to precursors for a suitable amount of time, such as two hours, and then allowed to dry, for example in a closed container.

TABLE I

| pH 2 | pH 5.5 | pH 7 | pH 10 |
| --- | --- | --- | --- |
| 0.18 m$^2$/g | 201 m$^2$/g | 62 m$^2$/g | 283 m$^2$/g |

Still further, the surface area can be varied at the same pH by varying the exposure time to the precursor, which as stated above may be, for example, TMOS. Typical surface areas obtained for water exposed for 1 hr is 700 m$^2$/g and for exposures exceeding 8 hrs is 200 m$^2$/g.

The presently described process results in gel formation at the lipid head groups, with the result that thickness can be easily controlled and varied. Accordingly, the synthesis process described herein may be used to form ultrathin films, by which it is meant films that have a thickness of no more than 100 nm and typically between 10 and 100 nm. These ultrathin films may be formed from as few as 2-3 bilayers. Moreover, the composition of each layer may be specifically directed, for example, one could form a film having alternating layers of silica and lipids.

For example, and again as shown in FIG. 20, a hybrid phospholipid-silica thin film assembly can be prepared by spin-coating phospholipid (DMPC, DOPC, DOPE, EggPC, or any other zwitterionic lipid) directly from chloroform solution onto silicon wafers. The concentration and speed of lipids can be altered in order to get desired thickness of the lipids on the silicon wafer. These spin-coated wafers can then be exposed to silanol precursors TEOS and water (or HCl) vapors for a desired amount of time at a specific temperature using the techniques described herein. The resulting films can be characterized by Transmission electron microscopy and X-ray diffraction.

Figure 6:
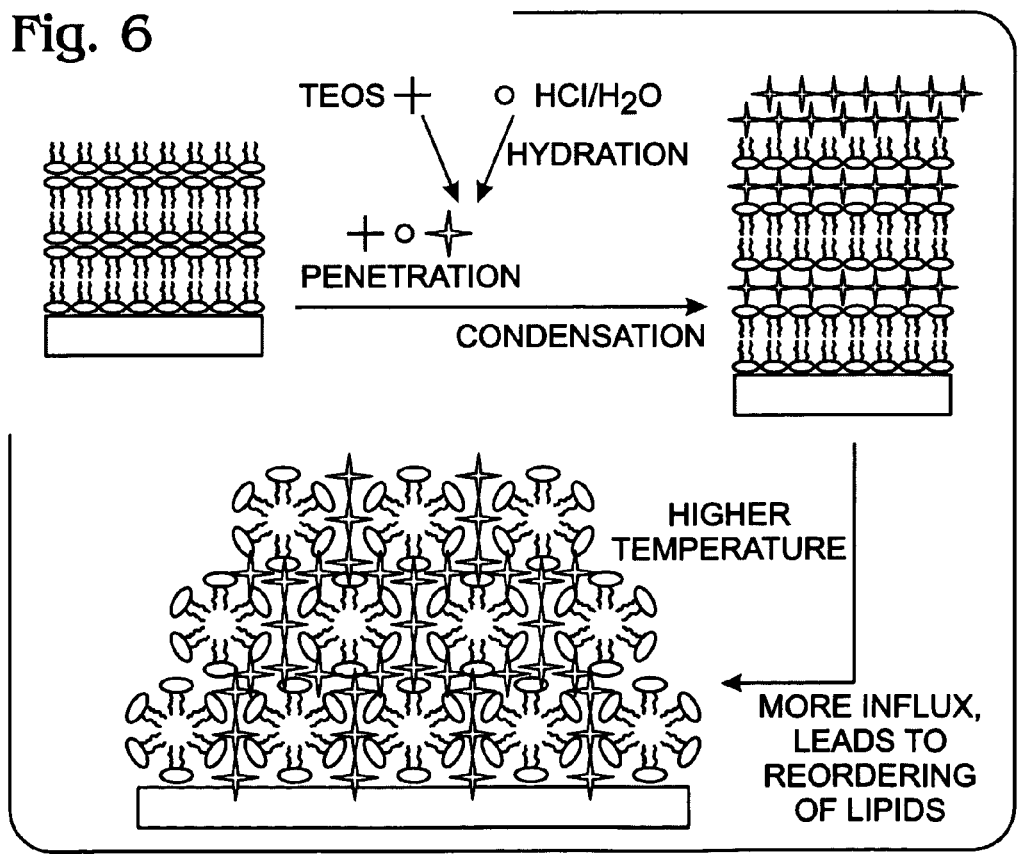
FIG. 6 is a schematic illustration depicting how the presently-described methods can be used to synthesize gels having different structural formations.

Turning now to FIG. 6, as stated above, the process described herein allows for the formation of various structures including lamellar or hexagonal structures and entrapped liposomes, as desired. According to one embodiment, lamellar assemblies are generally synthesized at lower temperatures (relative to the volatility of the precursor being used) such as room temperature or 37° C. with TMOS, or 60° C. with TEOS and hexagonal structures are obtained at higher temperatures, such as at 60° C. with TMOS and 90° C. with TEOS. In some embodiments, HCl may be included in the reaction chamber in order to help the rate of condensation (and thus gel formation.) However, the addition of HCl is not necessary, as gel formation will proceed with water alone. Liposomes can be entrapped in bulk by introducing a liposome-containing buffer into the reaction chamber.

Because the synthesis process described herein may be conducted at any desired pH, ionic strength, and temperature, the conditions may be selected in order to maintain (or effect) the biological activity of a biological species being incorporated into the gel. Accordingly a wide variety of biological species may be immobilized using the techniques described herein. Examples of suitable biological species include enzymes, proteins, peptides, nucleic acids, polysaccharides, trans-membrane proteins and peptides, bacteria, cells, and biomolecular assemblies including light harvesting complexes such as chlorosomes and chloroplasts, mitochondria, planar lipid bilayers, organelles, viruses, and even plants. Other suitable biological species include biological species having a lipid supramolecular architecture such as liposomes, unilamllar vesicles, multilamellar vesicles, supported lipid bilayers, black lipid bilayers, suspended lipid bilayers, Langmuir films, lipid stabilized microbubbles, and three-dimensional lipid phases; lipid-protein supramolecular architectures such as ion channels, ion-pumps, molecular pumps, and cellular membranes; protein supramolecular architectures; lipid-protein-bioorganic supramolecular assembles; lipid protein-bioinorganic supramolecular assemblies; organic polymer assemblies such as layer-by-layer structures; species capable of performing selective ion transfer such as ion channels, gramicidin, and neomycin; species capable of performing active transport such as bacteriorodopsin.

While in some embodiments the biological species may be provided in the initial aqueous solution so that they are incorporated into the gel as it is being formed, in other embodiments the biological species may be incorporated into a partially formed gel. In this case, the biological species may be provided in a solid phase. Examples of suitable solid phase biological species include, but are not limited to functional biomolecules that are transiently stable in solid phase, functional supramolecular architectures that are transiently stable in solid phase, multilamellar stacks, cells that are transiently stable in solid phase, fullerenes, carbon-nanotubes, and the like. A better understanding of the various types of species that may be immobilized and the structures that may be formed using the techniques described herein may be found by reviewing the Examples below.

It will additionally be understood that the methods of the present disclosure may be used to incorporate non-biologicals such as carbon nanotubes, nanoparticles and fullerenes into gels. In some embodiments, additional of non-biologicals can make the gels conductive in nature.

Gels formed using the presently described system are extremely stable. For example, gels formed using the process described herein and stored in air tight containers have maintained their structure and biological functionality for up to 6 months and longer periods of time are expected to yield similar results. Upon drying, the gels typically result in glass-like materials due to water loss.

As stated above, the gels formed using the techniques described above may include a wide variety of biologically active agents embedded or immobilized within the gel. Under certain conditions, biological reactions involving embedded agents may take place much more slowly than under in situ (or even other in vitro) conditions. For example, reactions that have previously taken place on the order of a mili- or microsecond, may be slowed down to the order of minutes. Accordingly, gels formed using the above-described techniques may be used to monitor and observe the mechanisms of a variety of biological reactions that have been previously difficult or even impossible to study.

Under some conditions, the gelation process described herein may be reversible. For example, we have demonstrated that the process may be reversed at alkaline pH, where gels placed in alkaline buffer will dissolve due to increased solubility of silica at higher pH.

Furthermore, due to the high level of stability demonstrated in the gels formed using the techniques described herein, gels of the presently disclosure may serve as a unique storage format for a variety of biological agents and substances including, for example, blood. As described in greater detail in the Example section below, biological agents stored in gels formed using the techniques described herein maintained biological activity for at least 180 days without refrigeration and for at least 120 days with refrigeration. Moreover, this may not be anywhere close to the limit of the shelf life for these gels. It will be appreciated that this would be of extreme benefit to researchers and practitioners in third world regions, recent disaster zones, or other areas where more traditional storage systems may be impractical or even impossible.

Furthermore, gels of the present disclosure may be formed into a novel drug delivery system wherein biologically active drug agents, for example contained in liposomes that have been encapsulated in a silica-based "pill" or other ingestible structure, can be ingested by a patient and the gel specifically structured to dissolve in a given target location. For example, it is known that silica dissolves in the duodenum and intestines but not in the stomach due to the different pH levels in each of these regions, accordingly, an ingestable gel could be formed that is designed to travel intact through the stomach and then dissolve, thereby release its biologically active payload, in the duodenum and intestines. Other suitable uses for the gels of the present disclosure include, but are not limited to functional layers in sensing systems, power sources such as photovoltaic devices, batteries or fuel cells, and integrated sensor-power source systems. Other uses or techniques that may be suitable for use with the methods, gels, and films described herein may be found by reference to U.S. patent application Ser. No. 11/690,922, which is hereby incorporated by reference.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Example I

Immobilization of Horseradish Peroxidase (HRP)

HRP as lyophilized powder and 3,3',5,5'-Tetramethylbenzidine (TMB) liquid substrate were purchased from Sigma-Aldrich, St. Louis, Mo., USA. HRP was dissolved in acetate buffer pH 5.5 at a concentration of 1 μg/ml. 1 ml of resulting solution was placed in a vial. This solution was placed in a closed container with another vial containing 0.2 ml of TMOS. The container was placed at room temperature in a fume hood. The buffer containing the HRP enzyme gelled in approximately 2 hrs.

These gels were tested as formed by adding 200 μl of TMB substrate. The gel developed a blue reaction product that can be read at 370 or 655 nm. An endpoint assay for the reaction was performed by adding acid, forming a yellow reaction product that can be read at 450 nm. These gels were also placed in refrigerator for 1, 7, 15, 30, and 60 120 and 180 days. The gels were tested by first bringing them to room temperature and using the procedure mentioned above at the identified day (i.e. 1, 7, 15, 30, 60, 120 and 180 days). The gels showed a clear indication of active HRP by forming the blue reaction product at all time points, indicating that the HRP was active even after 180 days. The gels were also placed at room temperature for 1, 7, 15, 30, 60, 120 and 180 days. Again, the HRP maintained activity at all time points, including at the 180-day time point.

Quantitative results were obtained using an alternative gelling approach. Indium tin oxide (ITO) coated glass slides were purchased from Sigma-Aldrich. A specific amount of 10 g/ml solution of HRP in acetate buffer was placed on ITO coated glass slides. These slides were exposed to vapors of TMOS using sonication in a closed container for 5 minutes. The gels were formed in 30 minutes. These gels were subjected to electrochemical testing in acetate buffer. The slides showed a clear response upon addition of peroxide to the buffer. Chronoamperometric measurements were made in acetate buffer pH 5.5 using a three electrode system. Ag/AgCl electrode and platinum wire were used as reference and counter electrode. A potential of −0.2 V was applied to the working enzyme coated ITO electrode. It was followed by a slight increase (tail) in negative current due to the reduction of peroxide on ITO electrode, over a longer period of time. Electrode coated with gel without the enzyme showed no sharp increase in current; however a slight increase (tail) in negative current was observed for this electrode. These results suggest that the protein is active even when immobilized in gels.

Example II

Thin and Ultra-Thin Film Formation

We have synthesized robust hybrid thin films (10-100 nm). Lipid coated silicon wafers are exposed to the vapors at varying temperatures leading to the formation of hybrid lamellar films. Typically, lipids are dissolved in chloroform at a concentration of 20 mg/ml. The resulting solution is spin-coated on clean silicon wafers at varying speeds of 1000-3000 RPM. These lipid coated samples are exposed to vapors of silanol precursors TMOS or TEOS and IN HCl at 37° C., 60° C. or 90° C. The time these wafers are exposed varies from 1 hr to 18 hrs. Ultra thin films can also be synthesized at room temperature and other temperatures without HCl. Lipid coated wafers are exposed to silanol vapors and water vapors resulting in lamellar thin films. In order to incorporate proteins in these robust materials we have used two different approaches. Gramicidin is dissolved in methanol at a concentration of 4.8 mg/ml. 300 μl of this solution is added to 1 ml of 20 mg/ml of chloroform. The resulting mixture is spin-coated on clean silicon wafers. Alternatively, 20 mg/ml of lipids in chloroform are dried under nitrogen, followed by exposure to vacuum for 2 hrs. A corresponding amount of gramicidin is added to the dried lipids. 1 ml of iso-propyl alcohol is added to the dried lipids. This solution is spin-coated on hydrophilic silicon wafers. The wafers are first cleaned in acetone solution for 5 minutes, followed by sonicating in methanol for 5 minutes. The wafers are rinsed with DI water and finally cleaned in a plasma cleaner for 2 minutes.

Figure 7:
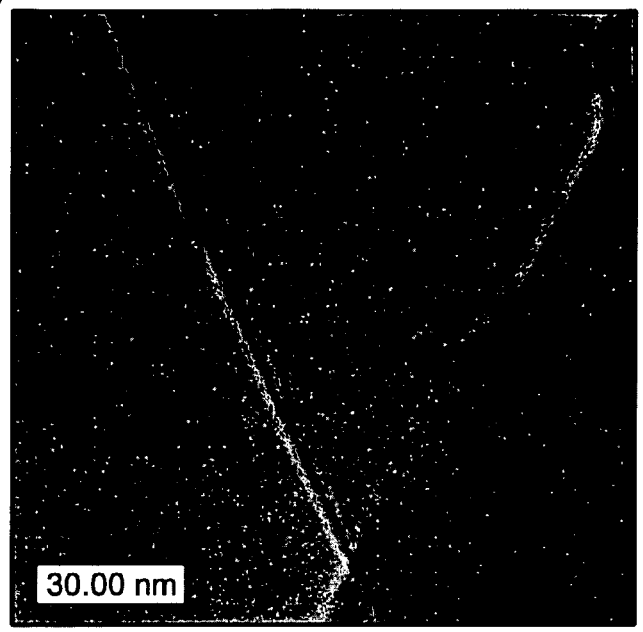
FIG. 7 is a TEM micrograph of a lamellar hybrid ultra thin film synthesized according to one embodiment of the present invention.
Figure 8:
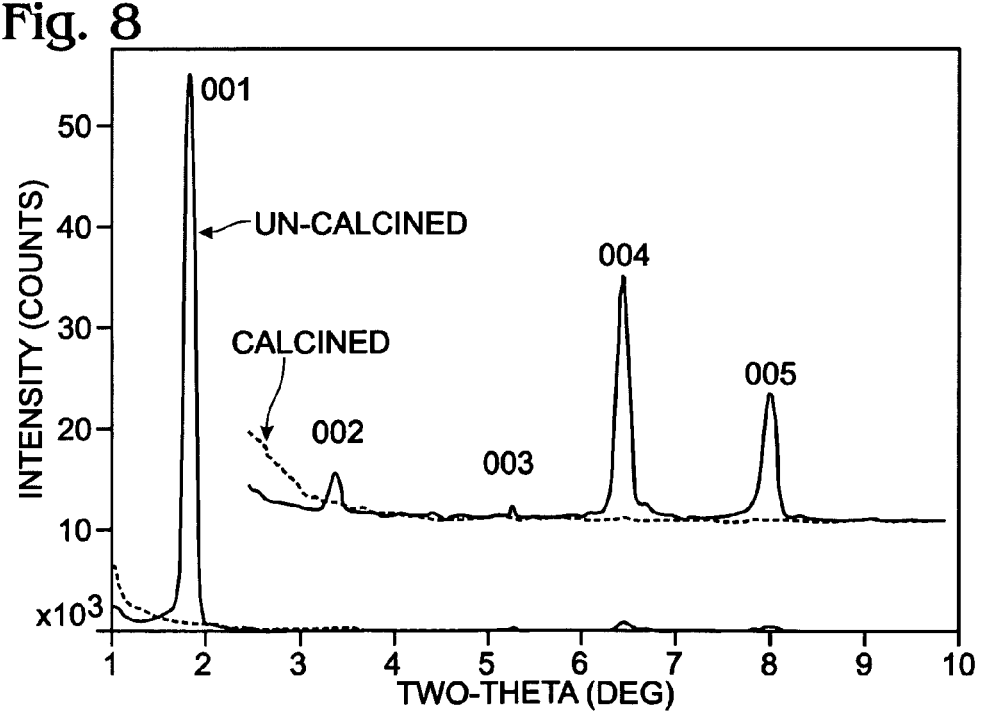
FIG. 8 is a graph depicting the corresponding X-ray diffraction patterns of a film before and after calcination.
Figure 9:
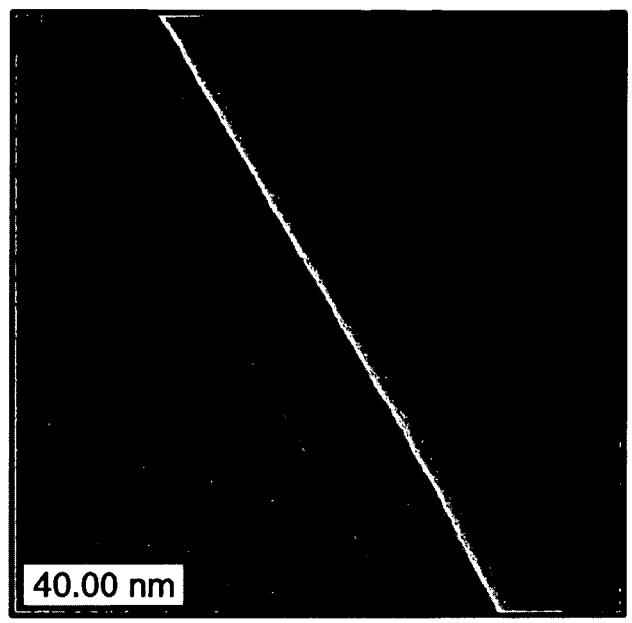
FIG. 9 is a TEM micrograph of DMPC-silica film synthesized according to an embodiment of the present invention.

FIG. 7 shows a TEM micrograph of a lamellar hybrid ultra thin film synthesized at 60° C. for 2 hrs using TEOS as a precursor. FIG. 8 shows a corresponding X-ray diffraction (XRD) pattern of the films before and after calcination. The pure lipid XRD pattern shows a d-spacing of 50.4 Å. An increase in d-spacing of 4 Å is observed after exposure to silanol precursors vapors for 2 hrs. The peaks are in ratio of 1:2:3:4 clearly indicating the presence of lamellar structure. The collapse of structure upon calcinations validates the lamellar structure. Lipid-silica films were synthesized using a similar process at 90° C. X-ray diffraction indicated a d-spacing of 58 Å. TEM reveals the structure to be hexagonal in nature. After calcination shrinkage is observed and d-spacing is decreased by 4 Å. FIG. 9 shows a TEM micrograph of DMPC-silica film.

Table II shows the results obtained using the vaporization process at two different temperatures.

TABLE II

| Lipid* | d-spacing (Å) | | | |
|---|---|---|---|---|
| DMPC | 60° C. | Phase | 90° C. | Phase |
| Before Calcination | 54 | Lamellar | 58 | Hexagonal |
| After Calcination | Nil | Confirm Lamellar | 54 | Shrinkage Hexagonal |

Ultra thin films can be obtained by varying the speed of coating and the concentration of the lipids in the chloroform solution and is confirmed by ellipsometry. Table III summarizes the results obtained by varying the concentration at a speed of 3000 RPM. The thickness increases after exposure to TEOS vapors for varying amount of time. We have incorporated gramicidin and bacteriorhodopsin in these systems. Detailed investigations have been made using X-ray diffraction and Neutron reflectivity.

TABLE III

| DMPC | 20 mg/ml Å | 10 mg/ml Å | 5 mg/ml Å | 2.5 mg/ml Å | 1.25 mg/ml Å |
|---|---|---|---|---|---|
| 0 hr | 1020 | 600 | 310 | 300 | 100 |
| 1 hr (C/S) | 1420/532 | 859/681 | 545/93 | 409/70 | 151/15 |
| 16 hr | — | — | 526/262 | — | 330/42 |

Figure 10:
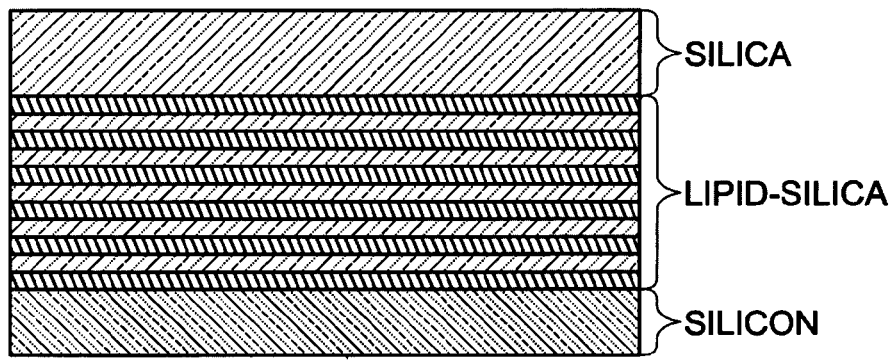
FIG. 10 is a schematic illustration of the cross-section of a film synthesized according to an embodiment of the present invention.

The schematic representation of the final structure indicated the formation of lamellar structures in the initial exposure. Upon increasing the exposure time, a silica film starts depositing on the silicon wafer as seen in FIG. 10.

Figure 11:
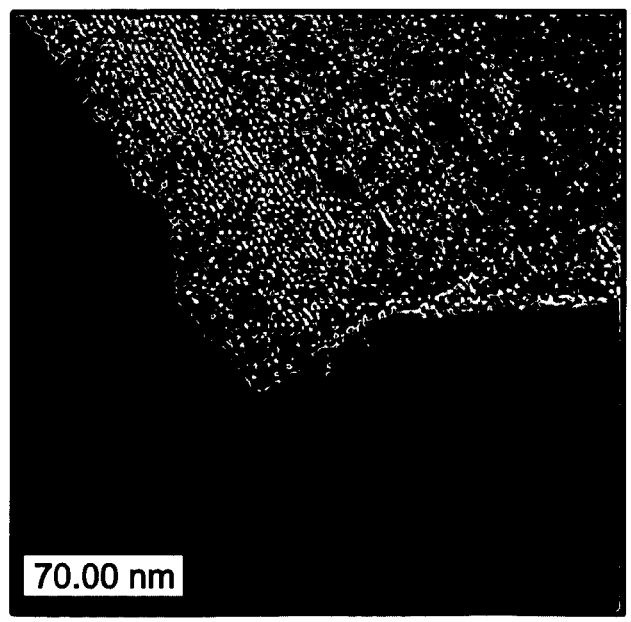
FIG. 11 is a TEM micrograph of a hexagonal hybrid ultra thin film synthesized according to an embodiment of the present invention.
Figure 12:
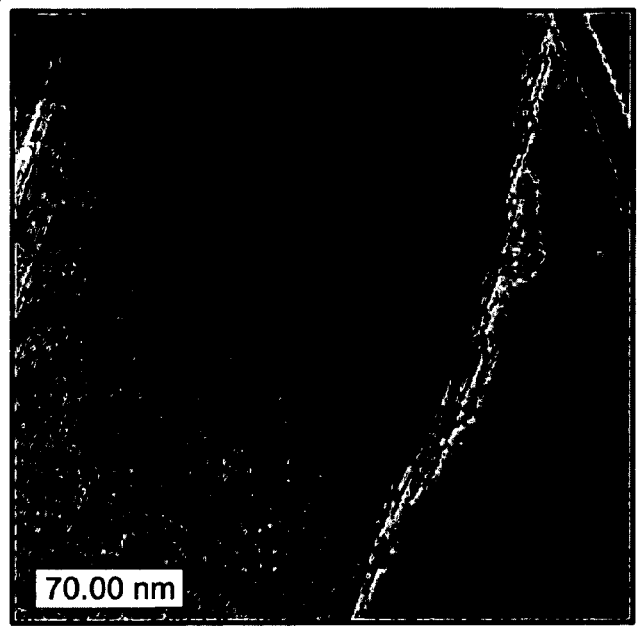
FIG. 12 is TEM micrograph of another hexagonal hybrid ultra thin film synthesized according to an embodiment of the present invention.

FIGS. 11 and 12 show TEM micrographs of a hexagonal hybrid ultra thin film. The lipids were exposed to TEOS vapors and 1 N HCl at 90° C. The increased temperature and presence of acid leads to an increase in the rate at which precursor vapors are formed and also increases the rate at which it hydrolyses and condenses. We believe in order to incorporate this huge amount of TEOS vapors, the lipids have to adjust themselves, and they do it by hexagonally packing. As a result, the process goes from a lamellar to a hexagonal phase transition. It is important to note that TMOS vapors at 60° C. behave the same way. In essence, the vapors penetrate deeper and faster forcing the hexagonal reassembly. In contrast, at lower temperatures, the silica itself starts acting as a barrier thus preventing further penetration and maintaining the lamellar structure.

Figure 13:
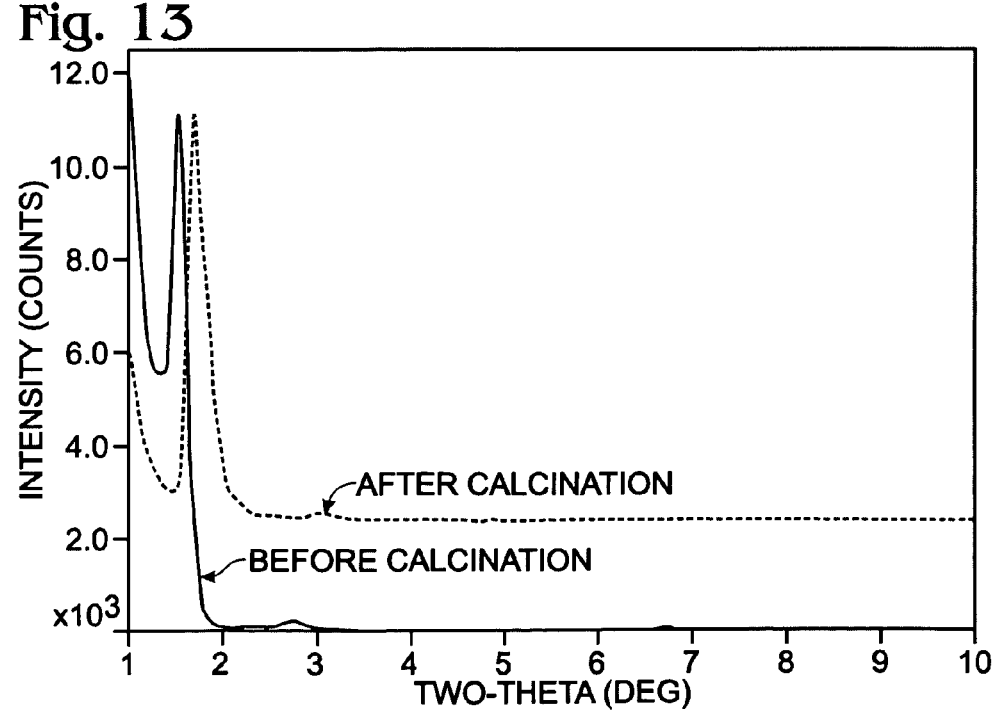
FIG. 13 is a graph depicting the corresponding X-ray diffraction patterns of a film before and after calcination.

The presence of a hexagonal structure is confirmed by looking at the TEM micrographs showing long range order viewing both sides. Also, after calcination, the film doesn't collapse, but only shrinks a small amount (in the depicted experiment, by 4 Å), as shown in FIG. 13 thus showing the complete condensation of the silica.

Example III

Liposome Entrapment

Figure 14:
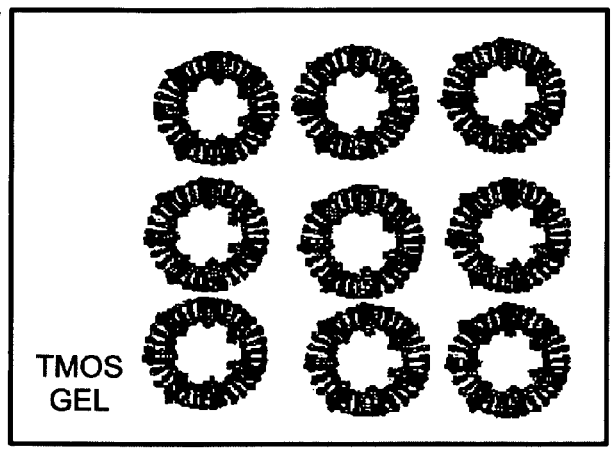
FIG. 14 is a schematic illustration showing how liposomes can be entrapped in a silica matrix.
Figure 15:
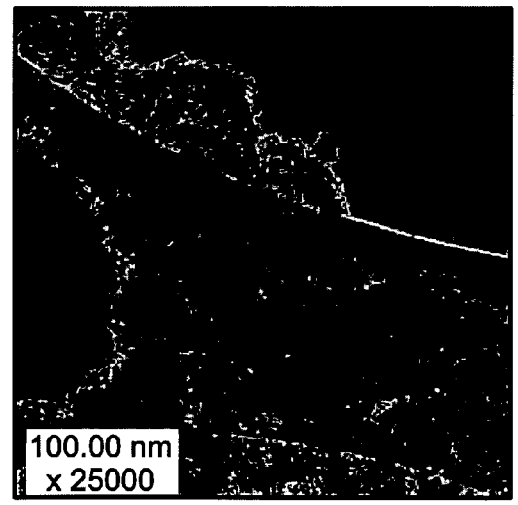
FIG. 15 is a SEM image of entrapped liposomes.

Sol-gel encapsulation of proteoliposomes has been achieved using this method as well. Typically, 1-20 mg of lipids are dissolved in 1 ml buffer. The lipids are hydrated for 1 hr. Liposomes are prepared using known methods including one of: sonication, extrusion or freeze thaw cycles. The liposomes in solution are exposed to vapors of TMOS for variable hours. FIGS. 14 and 15 show the entrapment of liposomes in a silica matrix. The liposomes may contain transmembrane proteins such as bacteriorhodopsin, which can be used to demonstrate active transport. Liposomes may also contain drugs, and can have specific trans-membrane proteins which can be delivered to a specific target organ.

Figure 16:
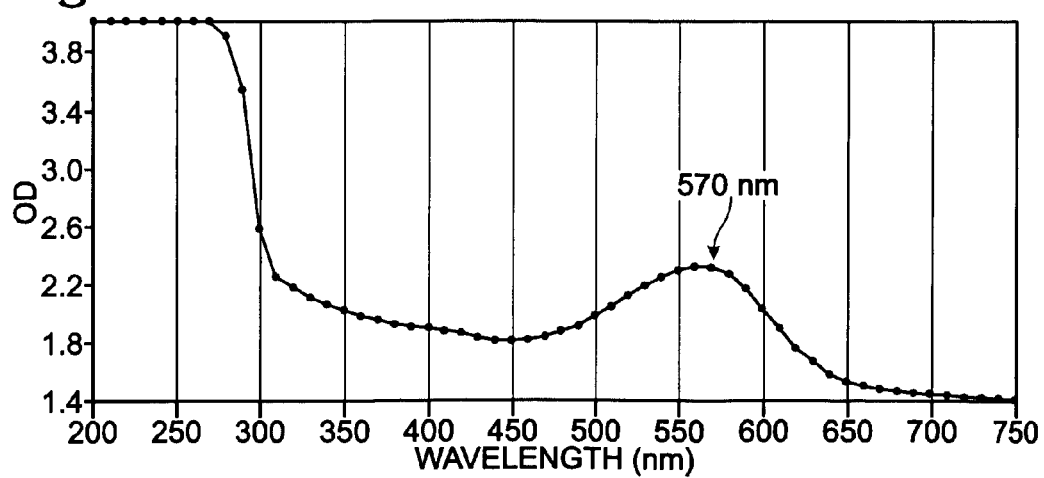
FIG. 16 is a graph depicting the UV-VIS spectrum of bacteriorhodopsin-containing liposomes over a period of 1 month.

Bacteriorhodopsin (purple membrane) has been incorporated in liposomes using sonication. The lipid mixture used was 4:1 DOPE: EggPC. DOPE has been shown to increase the incorporation of bacteriorhodopsin (bR). 10 mM pH buffer was used so that we could see the change in pH due to bacteriorhodopsin. After gelation, a few drops of buffer were added to the sample if the pH was not stable, for example due to improper contact with the pH electrode. The pH levels of gels containing the bR-incorporated liposomes before and after light exposure were measured and compared with the pH levels of blank-liposomes in gel before and after light exposure. Light with a yellow light filter was shined for 30 sec and a break for 60 sec was given. This was due to the fact that the blank-liposome gel in buffer was showing a slight decrease in pH, which was suspected to be due to a heat effect. The pH levels of the blank returned to baseline after exposure to light, whereas the pH levels of the bR-incorporated liposomes remained stable after the light was switched off, showing that there is very minimal leakage. Generally, the gels were kept in the dark for at least 1 hr before measurements for dark adaptation. Gels were stable for at least 3 weeks. After 3 weeks the proteoliposomes were intact in the gels, and an almost similar response was observed upon shining with light. However there was a slight decrease in activity of the proteoliposomes, i.e., the pH drop after shining of light decreased from 0.09 to 0.06. These results indicated the gels are capable of stabilizing liposomes over a long period of time with a minimal loss of activity FIG. 16 shows the UV-Vis spectrum of bacteriorhodopsin containing liposomes over a period of 1 month. The absorption peak at 570 nm indicates the presence of intact bacteriorhodopsin after gelation.

Figure 17:
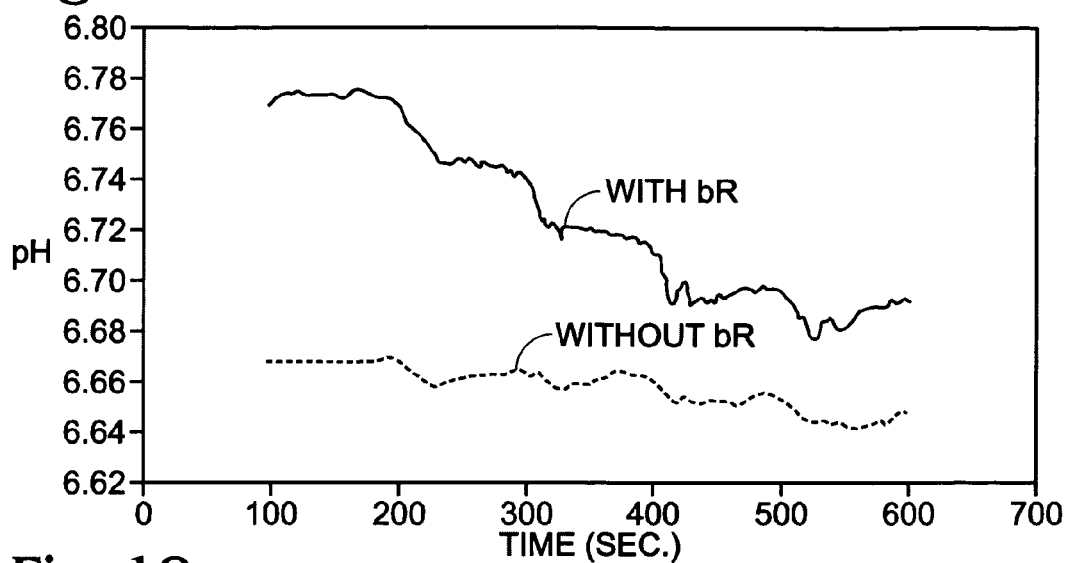
FIG. 17 is a graph depicting the change in pH in gels with or without bacteriorhodopsin upon exposure to light.

FIG. 17 shows the Δ pH response of the resulting gels with or without bacteriorhodopsin upon excitation by light. The Δ pH for the bacteriorhodopsin containing liposomes is four times higher as compared to pure liposomes upon excitation. These liposome solutions are placed at 25° C. under humid conditions and are stable over a period of month.

Example IV

Cell Immobilization and Micro-Reactors

We have successfully immobilized sea dwelling bacteria in our gels. $10^9$ cells $mL^{-1}$ of Cobetia marina from an overnight culture were centrifuged (10 min, micro centrifuge highest setting) and re-suspended in artificial seawater 3×. Final volume was 10 mL. Gels were made from 2 mL aliquots of suspended cells by exposing them to TMOS with and without glycerol for 2 hours.

After the gels solidified, we added 5 mL marine broth to each gel, mixed and grew overnight. Imaging phase contrast 63× magnification was carried out and it clearly indicated the presence of dividing bacteria.

This clearly indicates that the method is benign to the entrapment of bacteria and also compatible with an ionic strength of 4M salt.

We repeated the experiment, but instead of culturing, used a live dead assay (with Syto 60-abs 652, emission 678—red=live cells) and Cytox (ex. 504 em 523—green=dead cells) Gels formed at 37° C. had less number of cells, but most of them were alive, where as gels synthesized at 37° C. with glycerol, had large number of cells, but 113 of them were dead.

Based on both sets of data, we conclude that the best conditions are 37° C. with no glycerol, followed by 25° C. with glycerol. We suspect that 37° C. is nearing the upper limit of survival for C marina, thus heat shock responses have kicked in, allowing more cells to survive. However, as in most heat shock situations, these cells are somewhat stunted.

Example V

Planar Bilayers in Gels

Figure 18:
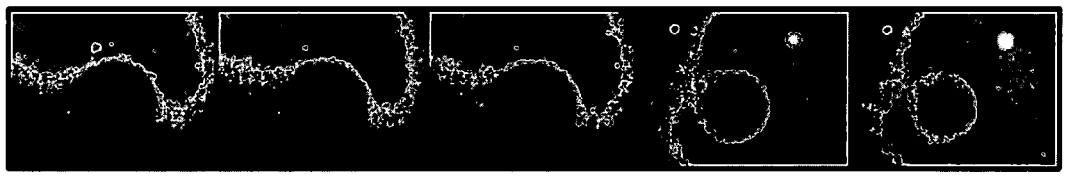
FIG. 18 depicts an immobilization of a planar bilayer.
Figure 19A:
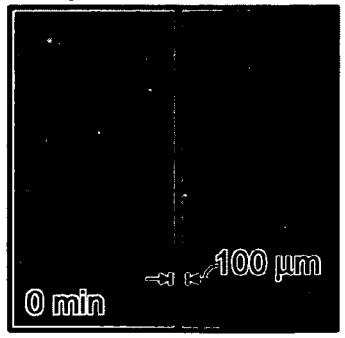
FIG. 19A shows the results of a photo bleaching experiment after 0 min.
Figure 19B:
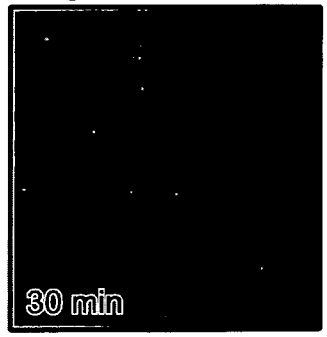
FIG. 19B shows the results of a photo bleaching experiment after 30 min.
Figure 19C:
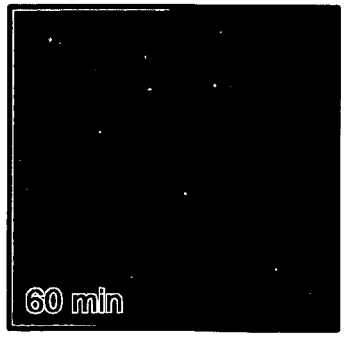
FIG. 19C shows the results of a photo bleaching experiment after 60 min.
Figure 19D:
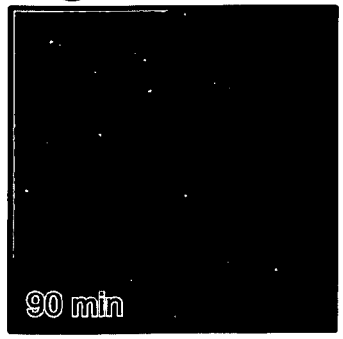
FIG. 19D shows the results of a photo bleaching experiment after 90 min.
Figure 19E:
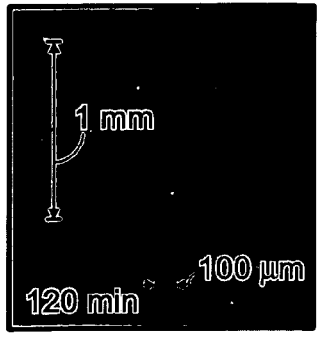
FIG. 19E shows the results of a photo bleaching experiment after 120 min.

FIG. 18 shows an immobilization of a planar bilayer. Lipid POPC:Bodipy DMPE were mixed in molar ratio of 100:1. A planar bilayer was prepared on clean silicon surface. Planar bilayers under buffer were exposed to silanol precursors for 2 hr. A spot measuring 20 microns was bleached and recovery measurements (FRAP-fluorescence recovery after photobleaching) were performed after certain times. The figures are taken at 0, 30, 60, 120 and 180 minutes. The recovery was observed indicating the fluidity of the lipids. But, as mentioned before, the recovery was an order slower than what would be expected in water.

Example VI

Multi-Lamellar Silica Assemblies

Multi-lamellar silica assemblies were synthesized using a procedure mentioned earlier. Briefly, Lipid POPC: NBDPE were mixed in molar ratio of 100:1 in chloroform. The resulting solution was spin-coated on silicon wafers. These lamellar assemblies were exposed to TMOS vapors at 37° C. for 1 hr. Fluorescence recovery after photo bleaching measurements were performed. A line measuring 60 micron×1.5 mm was bleached on the sample. (See FIGS. 19A-19E) Recovery was observed over a period of 2 hrs. These assemblies are very stable in water and air over a period of 1 month, the longest time we have characterized in our lab.

What is claimed is:

1. A method for forming a gel incorporating a functional biological species comprising:
    providing in a reaction chamber:
        a gel precursor in a first container; and
        an aqueous solution in a second container,
    providing suitable conditions such that the gel precursor is able to evaporate;
    allowing the evaporated gel precursor to associate with the aqueous solution;
    providing a first functional biological species;
    providing suitable conditions to allow for further condensation of the gel-aqueous solution, thereby allowing at least partial formation of a gel; and
    providing suitable conditions to allow for incorporation of the first functional biological species into the at least partially formed gel;
    wherein, the biological species maintains functionality while incorporated within the gel.

2. The method of claim 1 wherein the gel precursor is a silica precursor.

3. The method of claim 1 further comprising providing suitable conditions such that complete formation of the gel is achieved.

4. The method of claim 1 wherein the first biological species is a lipid supramolecular architecture.

5. The method of claim 4 wherein the lipid supramolecular architecture is selected from the group consisting of: liposomes, unilamllar vesicles, multilamellar vesicles, supported lipid bilayers, black lipid bilayers, suspended lipid bilayers, Langmuir films, lipid stabilized microbubbles, and three-dimensional lipid phases.

6. The method of claim 1 wherein the first biological species is a lipid-protein supramolecular architecture.

7. The method of claim 6 wherein the lipid-protein supramolecular architecture contains architectures selected from the group consisting of: ion channels, ion-pumps, molecular pumps, and cellular membranes.

8. The method of claim 1 wherein the first biological species is selected from the group consisting of protein supramolecular architectures, lipid-protein-bioorganic supramolecular assembles, lipid protein-bioinorganic supramolecular assemblies.

9. The method of claim 1 wherein the first biological species contains biopolymer assemblies.

10. The method of claim 1 wherein the first biological species is an organic polymer assembly.

11. The method of claim 9 wherein at least one of the biopolymer assemblies comprises layer-by-layer structures.

12. The method of claim 1 wherein the first biological species is a functional protein.

13. The method of claim 1 wherein the biological species is a cell.

14. The method of claim 1 wherein the biological species is an organelle.

15. The method of claim 1 wherein the biological species is a virus.

16. The method of claim 1 wherein the biological species is capable of performing selective ion transfer.

17. The method of claim 1 wherein the biological species is an ion channels.

18. The method of claim 1 wherein the biological species is capable of performing active transport.

19. The method of claim 1 wherein the biological species is bacteriorhodipsin.

20. The method of claim 1 wherein the biological species is a chloroplast.

21. The method of claim 1 wherein the biological species is a bacteria.

22. The method of claim 1 wherein the biological species is an enzyme.

23. The method of claim 1 wherein the biological species is contained in the aqueous solution.

24. The method of claim 1 wherein the biological species is incorporated into the gel after the at least partially formed gel is at least partially formed.

25. The method of claim 1 wherein the biological species is in solid phase.

26. The method of claim 25 wherein the solid phase biological species is selected from the group consisting of functional biomolecules that are transiently stable in solid phase, functional supramolecular architectures that are transiently stable in solid phase, multilamellar stacks, and cells that are transiently stable in solid phase.

27. The method of claim 1 further comprising a non-biological species.

28. The method of claim 27 wherein the non biological species is a fullerene.

29. The method of claim 27 wherein the non-biological species is a carbon-nanotube.

30. The method of claim 1 comprising further processing the partially formed gel.

31. The method of claim 30 wherein the further processing comprises coating the partially formed gel onto a substrate.

32. The method of claim 31 further comprising spin-coating the gel onto a solid substrate.

33. The method of claim 1 further comprising reversing the process by exposing the formed gel to an alkaline solution.

34. The method of claim 1 wherein formation of the gel is performed at or above room temperature.

35. The method of claim 3 wherein complete formation of the gel is achieved in 6 hours or less.

36. The method of claim 3 wherein complete formation of the gel is achieved less than an hour.

37. The method of claim 1 further comprising selecting the pH conditions of the reaction in order to achieve a desired porosity of the gel.

38. The method of claim 1 wherein the resulting film is less than 100 nm thick.

39. The method of claim 1 wherein the resulting film is formed from less than 3 bilayers.

* * * * *